(12) United States Patent
Takahashi

(10) Patent No.: US 9,337,901 B2
(45) Date of Patent: May 10, 2016

(54) MEDICAL IMAGE DIAGNOSIS APPARATUS

(71) Applicants: Kabushiki Kaisha Toshiba, Tokyo (JP);
Toshiba Medical Systems Corporation,
Otawara-shi (JP)

(72) Inventor: Katsuo Takahashi, Nasushiobara (JP)

(73) Assignees: Kabushiki Kaisha Toshiba, Tokyo (JP);
Toshiba Medical Systems Corporation,
Otawara-shi (JP)

( * ) Notice: Subject to any disclaimer, the term of this patent is extended or adjusted under 35 U.S.C. 154(b) by 272 days.

(21) Appl. No.: 13/758,029

(22) Filed: Feb. 4, 2013

(65) Prior Publication Data
US 2013/0200842 A1   Aug. 8, 2013

(30) Foreign Application Priority Data

Feb. 8, 2012 (JP) ................................ 2012-024799

(51) Int. Cl.
*H02J 7/00* (2006.01)
*A61B 5/05* (2006.01)
(Continued)

(52) U.S. Cl.
CPC .............. *H04B 5/0037* (2013.01); *A61B 6/548* (2013.01); *A61B 8/56* (2013.01); *H02J 7/025* (2013.01); *H04B 5/0075* (2013.01); *H02J 5/005* (2013.01)

(58) Field of Classification Search
CPC ........ H02J 5/005; H02J 7/025; H04B 5/0075; H02B 5/0037; A61B 6/548; A61B 8/56
USPC ............................ 320/108, 166; 600/424, 509
See application file for complete search history.

(56) References Cited

U.S. PATENT DOCUMENTS 7,456,606 B1 *  11/2008  Legg ............................ 320/108
7,729,742 B2 *   6/2010  Govari ......................... 600/424
(Continued)

FOREIGN PATENT DOCUMENTS

CN     101765405 A    6/2010
JP     2008-206219    9/2008
(Continued)

OTHER PUBLICATIONS

Office Action and Search Report issued on Sep. 1, 2014 in the corresponding Chinese Patent Application No. 201310047384.8 (with Translation of category of cited documents).

(Continued)

*Primary Examiner* — Helen Rossoshek
(74) *Attorney, Agent, or Firm* — Oblon, McClelland, Maier & Neustadt, L.L.P.

(57) ABSTRACT

The medical image diagnosis apparatus has a body, a power transmitting part, a power receiving part, and a device. The power transmitting part is housed in the body, has a transmission coil, and generates an oscillating field due to resonance from the transmission coil upon receiving electric power. The power receiving part has a reception coil, resonates with a frequency substantially equal to the resonant frequency of the transmission coil, and generates electric power upon receiving the oscillating field. The device houses the power receiving part, deriving organization information through operation via non-contact with the body by electric power from the power receiving part. The apparatus comprises a status checker and a controller that determines whether or not electric power should be generated depending on at least one of the statuses to control the generation of electric power by the transmission coil.

14 Claims, 5 Drawing Sheets

(51) Int. Cl.
  *H04B 5/00* (2006.01)
  *A61B 6/00* (2006.01)
  *A61B 8/00* (2006.01)
  *H02J 7/02* (2016.01)
  *H02J 5/00* (2016.01)

(56) References Cited

U.S. PATENT DOCUMENTS

| | | | |
|---|---|---|---|
| 8,391,953 B2 * | 3/2013 | Govari et al. | 600/424 |
| 8,581,444 B2 * | 11/2013 | Urano | 307/104 |
| 8,600,510 B2 * | 12/2013 | Forsell | 607/39 |
| 8,845,510 B2 * | 9/2014 | Zilbershlag | 600/16 |
| 8,861,678 B2 * | 10/2014 | Liu et al. | 378/91 |
| 8,922,065 B2 * | 12/2014 | Sun et al. | 307/104 |
| 2008/0169420 A1 | 7/2008 | Eguchi | |
| 2011/0057606 A1 * | 3/2011 | Saunamaki | 320/108 |
| 2011/0087337 A1 * | 4/2011 | Forsell | 623/23.68 |
| 2011/0121834 A1 * | 5/2011 | Soutome et al. | 324/318 |
| 2011/0196271 A1 * | 8/2011 | Forsell | 601/46 |
| 2011/0196435 A1 * | 8/2011 | Forsell | 606/86 R |
| 2012/0223709 A1 * | 9/2012 | Schillak et al. | 324/309 |
| 2012/0235636 A1 * | 9/2012 | Partovi | 320/108 |
| 2012/0242284 A1 * | 9/2012 | Wheatley et al. | 320/108 |
| 2013/0009609 A1 * | 1/2013 | Andersen et al. | 320/166 |
| 2014/0031607 A1 * | 1/2014 | Zilbershlag et al. | 600/16 |
| 2014/0218035 A1 * | 8/2014 | Okamoto | 324/322 |
| 2015/0038864 A1 * | 2/2015 | Kataoka et al. | 600/509 |
| 2015/0057653 A1 * | 2/2015 | Sugiyama | 606/34 |

FOREIGN PATENT DOCUMENTS

| | | |
|---|---|---|
| JP | 2010-016977 | 1/2010 |
| JP | 2010-158515 | 7/2010 |
| JP | 2011-507481 | 3/2011 |
| WO | WO 95/07109 | 3/1995 |
| WO | WO 2010/116441 A1 | 10/2010 |
| WO | WO2011/128969 | 10/2011 |

OTHER PUBLICATIONS

Japanese Office Action mailed Sep. 8, 2015 in Japanese Patent Application No. 2012-024799.

* cited by examiner

MEDICAL IMAGE DIAGNOSIS APPARATUS

CROSS-REFERENCE TO RELATED APPLICATION

This application is based upon and claims the benefit of priority from Japanese Patent Application No. 2012-024799, filed on Feb. 8, 2012; the entire contents of which are incorporated herein by reference.

FIELD

The embodiment relates to a medical image diagnosis apparatus.

BACKGROUND

A medical image diagnosis apparatus receives signals from a test body and derives the organization information thereof. Some medical image diagnosis apparatuses have a body as well as a device operating in cooperation with this. Exemplary medical image diagnosis apparatuses include an X-ray diagnosis apparatus, an MRI (Magnetic Resonance Imaging) apparatus, an ultrasound diagnosis apparatus, etc. As an example of the present device of the X-ray diagnosis apparatus, a wireless X-ray detector (wireless FPD (Flat Panel Detector)) is cited. As an example of the present device of the MRI apparatus, an RF coil unit is cited. As an example of the present device of the ultrasound diagnosis apparatus, an ultrasound probe is cited.

These devices operate with an electric power supply from the outside. A battery is mounted on the device wirelessly connected to the body. As a charging method of a battery, a non-contact charging method is known which uses electromagnetic induction from a mere coil.

DETAILED DESCRIPTION

Figure 1:
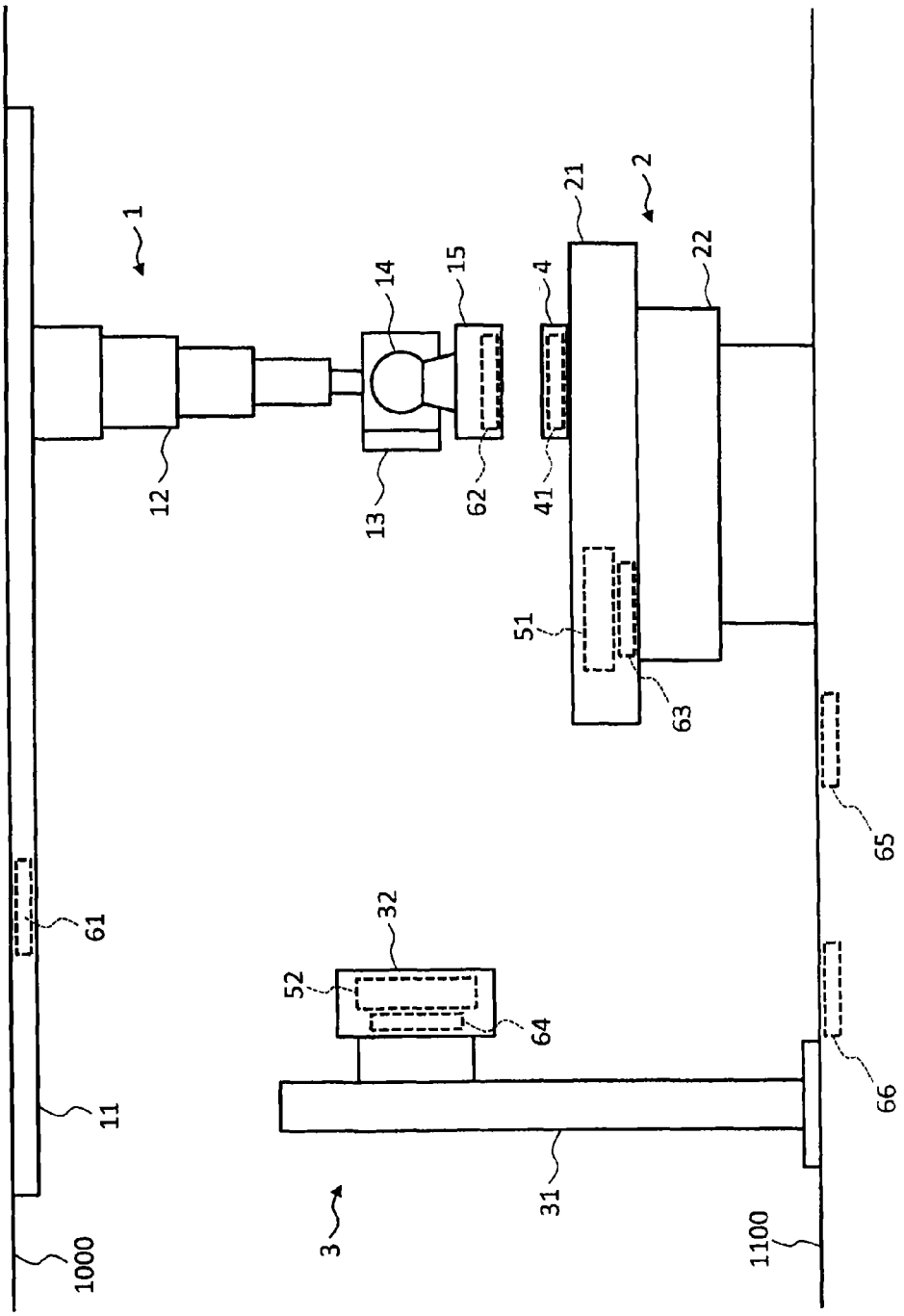
FIG. 1 illustrates an example of a configuration of a medical image diagnosis apparatus according to an embodiment.

The object of this embodiment is to provide a medical image diagnosis apparatus capable of preferably supplying electric power to a device operating in liaison with a body.

The medical image diagnosis apparatus according to the embodiment is an apparatus that receives signals from a test body and derives the organization information thereof so as to check the test body, the apparatus having a body, a power transmitting part, a power receiving part, and a device. The power transmitting part is housed in the body, has a transmission coil, and generates an oscillating field due to the resonance from the transmission coil upon receiving electric power from the outside. The power receiving part has a reception coil, resonates with a frequency substantially equal to the resonant frequency of the transmission coil, and generates electric power upon receiving the oscillating field generated by the transmission coil. The device houses the power receiving part therein, deriving the organization information through operation via non-contact with the body by electric power from the power receiving part. In addition, the apparatus comprises a status checker (a status checker) that derives at least one of the operation statuses (status) of the body and the device, and a controller (a controller) that determines whether or not electric power should be generated depending on at least one of the statuses of the body and the device, and based on the determination result, controls the generation of electric power by the transmission coil.

The medical image diagnosis apparatus according to the embodiment will be described with reference to the drawings.

The medical image diagnosis apparatus according to the embodiment has a body and a device that operates in liaison with this body. As such a medical image diagnosis apparatus, an X-ray diagnosis apparatus, an MRI apparatus, an ultrasound diagnosis apparatus, etc. are considered. This medical image diagnosis apparatus may be configured along with the conventional case except for a part relevant to electric power supply to be described later.

Exposing X-rays to the test body and detecting the X-rays transmitted through the test body, the X-ray diagnosis apparatus forms X-ray images of the test body based on its detection data. The above-described device is, for example, a wireless X-ray detector. In addition, the above-described body has a bed apparatus, an X-ray tube apparatus, a high voltage generating apparatus, a control system, an image processing system, a display system, an operation system, etc.

An MRI apparatus, utilizing a magnetic resonance phenomenon, collects the data in the test body and reconfigures the images in the test body based on this data. The above-described device, for example, is an RF coil used for imaging a predetermined region of the test body. In addition, the above-described body has a bed apparatus, a gantry, a control system, an image processing system, a display system, an operation system, etc.

The ultrasound diagnosis apparatus projects ultrasound waves to the test body and images inside the test body based on echo signals derived through the reception of reflected waves thereof. The above-described device, for example, is an ultrasound probe that transmits and receives ultrasound waves. In addition, the above-described body has a control system, an image processing system, a display system, an operation system, etc.

Hereinafter, the X-ray diagnosis apparatus to supply electric power via non-contact with the body in particular will be described in detail; however, a similar non-contact electric power supply means can be applied to other types of medical image diagnosis apparatuses.

[Apparatus Configuration]

The configuration examples of an X-ray diagnosis apparatus according to an embodiment will be illustrated in FIGS. 1 to 4.

(Summary)

Figure 2:
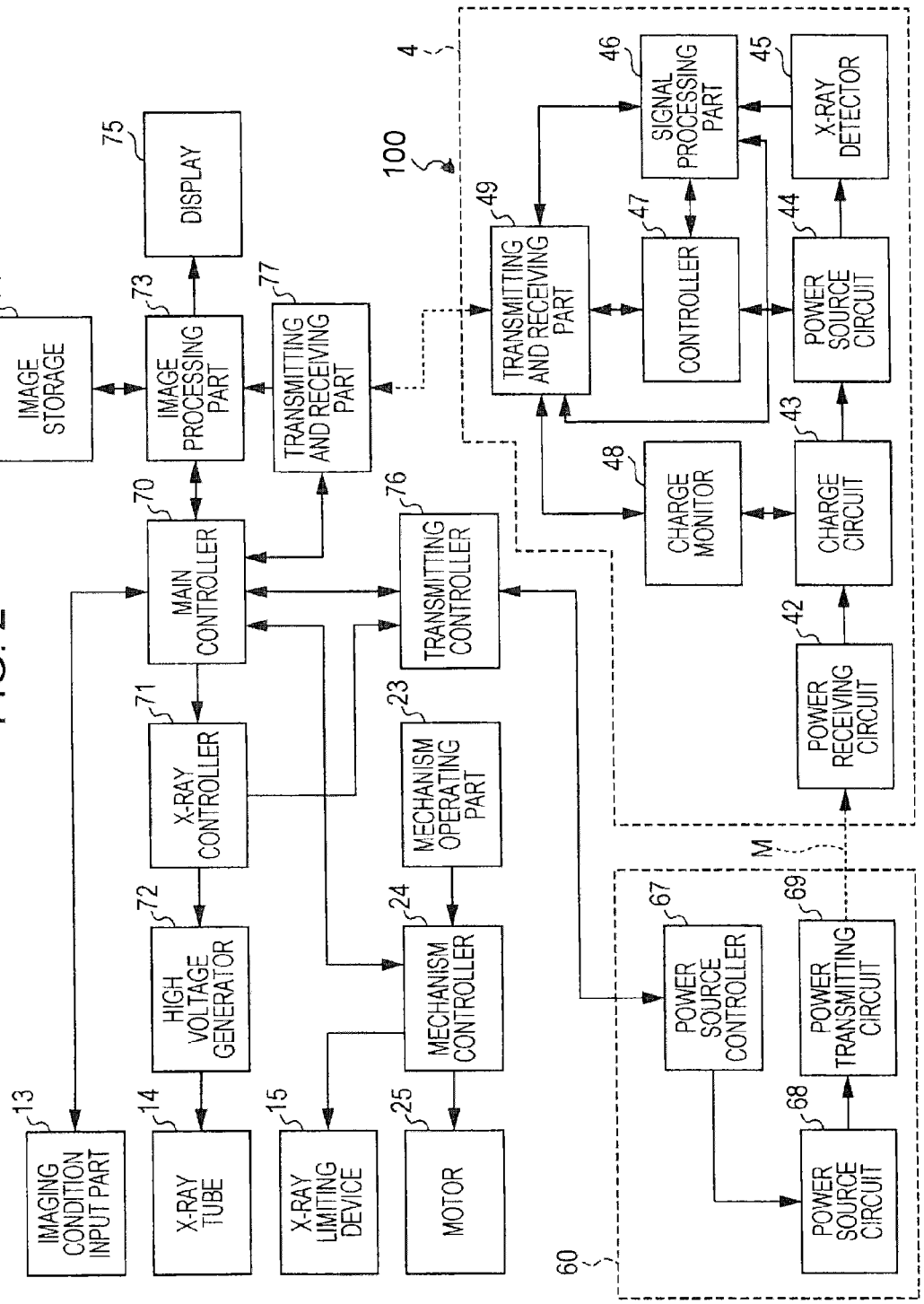
FIG. 2 illustrates an example of a configuration of a control system of the medical image diagnosis apparatus according to the embodiment.

As illustrated in FIG. 1, this X-ray diagnosis apparatus has an overhead running X-ray irradiating apparatus 1, an imaging table (bed apparatus) 2 for the supine position, an upright position imaging table 3, and a wireless X-ray detector (FPD) 4, respectively. Further, this X-ray diagnosis apparatus has a high voltage generator 72, a control system, an image processing system, a display system, an operation system, etc. that are illustrated in FIG. 2.

The overhead running X-ray irradiating apparatus 1 outputs X-rays for imaging.

The overhead running X-ray irradiating apparatus 1 has a rail 11, a support mechanism 12, an imaging condition input part 13, an X-ray tube 14, and an X-ray limiting device 15, respectively. The rail 11 is disposed on the ceiling 1000 of a laboratory. The support mechanism 12 has its upper end engaged to the rail 11 so as to be movable along the rail 11. The support mechanism 12 is configured such that it is capable of vertically expanding and contracting. On the lower end of the support mechanism 12, the imaging condition input part 13, the X-ray tube 14, and the X-ray limiting device 15 are disposed, respectively. The imaging condition input part 13 is used for setting imaging conditions by a user. The imaging conditions refer to various parameters to be applied to the X-ray imaging and include the imaging protocol, X-ray conditions, etc. The imaging protocol is set depending on the imaging operative method, the imaging region, the imaging field, the thickness of a body, etc. The X-ray conditions include the tube voltage (kV), tube current (mA), pulse width (imaging time, msec), etc. The X-ray tube 14 outputs X-rays corresponding to the imaging conditions. The X-ray limiting device 15 limits the irradiation range of the X-rays output from the X-ray tube 14 corresponding to the imaging region. The rail 11 or the ceiling 1000 is provided with a power transmitting apparatus 61. In addition, the X-ray limiting device 15 is provided with a power transmitting apparatus 62. The power transmitting apparatuses 61 and 62 will be described later.

The supine position imaging table 2 is used for X-ray imaging in the supine position. The supine position imaging table 2 is placed on the floor 1100 of the laboratory. The supine position imaging table 2 has a top plate 21 on which the test body is mounted and a driving part 22 for moving the top plate 21. An FPD holder 51 and a power transmitting apparatus 63 are disposed on the top plate 21. A wireless X-ray detector 4 is fitted on the FPD holder 51. The power transmitting apparatus 63 will be described later.

The upright position imaging table 3 is used for X-ray imaging in the upright position. The upright position imaging table 3 has a support part 31 extending upwards from the floor 1100 and a body part 32 supported by the support part 31. The body part 32 is provided with an FPD holder 52 and a power transmitting apparatus 64. The wireless X-ray detector 4 is fitted on the FPD holder 52. The power transmitting apparatus 64 will be described later.

On the floor 1100, a power transmitting apparatus 65 arranged in the vicinity of the supine position imaging table 2 and a power transmitting apparatus 66 in the vicinity of the imaging table 3 are disposed.

The wireless X-ray detector 4 is a wireless X-ray flat plane detector (FPD) that generates electric signals by detecting X-rays. The wireless X-ray detector 4 is used while being fitted to FPD holders 51, 52. In addition, the wireless X-ray detector 4 is used while mounted on the top plate 21. The operation of the wireless X-ray detector 4 is controlled via wireless communication with the body. In addition, the data received from the wireless X-ray detector 4 is transmitted to the body via wireless communication. The wireless X-ray detector 4 is provided with a power receiving apparatus 41. The power receiving apparatus 41 generates electric power upon receiving oscillating fields from the power transmitting apparatuses 61 to 66. The device (100 in FIG. 2) is provided with this wireless X-ray detector 4 and is operated using the electric power generated by the power receiving apparatus 41 to receive the organization information thereof. For example, this electric power is used for the detection of X-rays, etc. The details of the power receiving apparatus 41 will be described later. The body is correctively referred to each apparatus to house any of the power transmitting apparatuses 61 to 66, and as the body, for example, the overhead running X-ray irradiating apparatus 1, the supine position imaging table 2, and the upright position imaging table 3 are cited. The body houses the power transmitting apparatus 60; however, the body itself is configured without the wireless X-ray detector 4 and the power transmitting apparatus 60 illustrated in FIG. 2.

(Control System)

Figure 3:
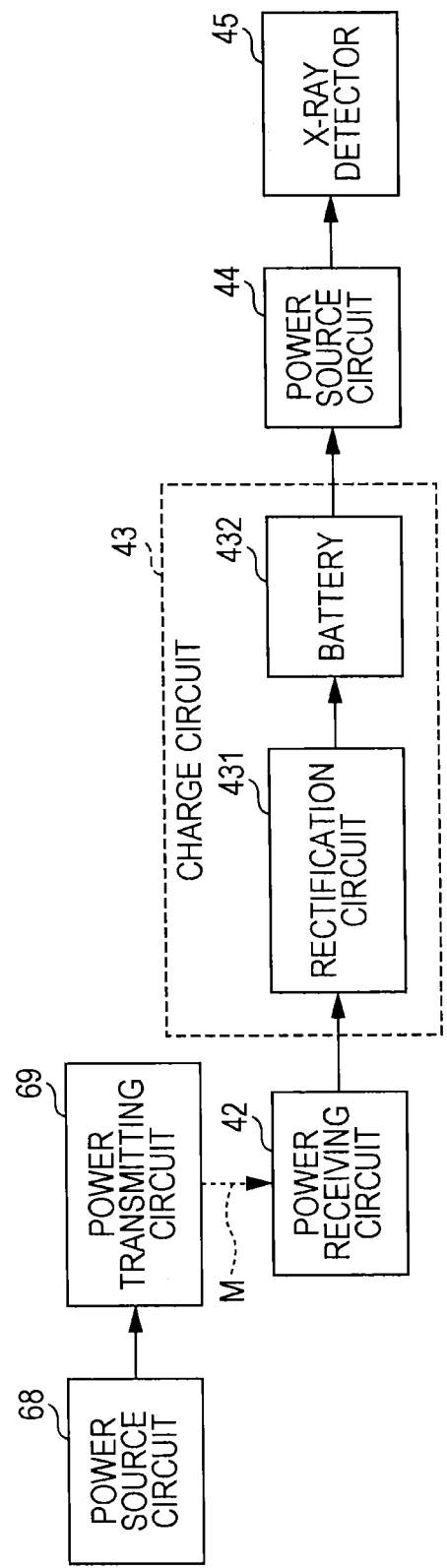
FIG. 3 illustrates an example of a configuration of a control system of the medical image diagnosis apparatus according to the embodiment.

Further, with reference to FIG. 2 and FIG. 3, a control system of the X-ray diagnosis apparatus will be described. The control system of the X-ray diagnosis apparatus is mainly composed of a main controller 70. The main controller 70 controls each part of the apparatus based on computer programs and various data. The main controller 70 receives the imaging conditions set by the imaging condition input part 13. The main controller 70 carries out the control corresponding to this imaging condition. In addition, the main controller 70 receives parameters according to the image processing and a display system. These parameters include the settings for a look up table (LUT), the window level (wl), and the window width (ww), etc.

The X-ray controller 71 controls a high voltage generator 72 upon receiving control signals based on the imaging conditions from the main controller 70. The high voltage generator 72 generates a high voltage for causing the X-ray tube 14 to generate X-rays. The X-ray tube 14 outputs X-rays upon receiving a high voltage from the high voltage generator 72.

A mechanism controller 24 receives control signals from the main controller 70 and operation signals according to the content set by a mechanism operating part 23. The mechanism controller 24 operates a motor 25 as an actuator of the driving part 22 based on the control signals and the operation signals. Due to this control, the driving part 22 3-dimensionally moves the top plate 21. In addition, the mechanism controller 24 controls the X-ray limiting device 15 based on the control signals from the main controller 70. Thereby, the irradiation ranges of the X-rays are changed.

An image processing part 73 carries out a variety of image processing. This image processing includes the processing for the display of LUT, Wl, ww, etc. The image data having the processing for display applied is transmitted to a display 75 and the images thereof are displayed. In addition, the image data processed by the image processing part 73 is stored in the image storage 74.

A power transmitting controller 76 controls the power transmitting apparatus 60 based on the control by the main controller 70. Further, the power transmitting apparatus 60 illustrated in FIG. 2 indicates respective power transmitting apparatuses 61 to 66 illustrated in FIG. 1. The power transmitting apparatus 60 has a power source controller 67, a power source circuit 68, and a power transmitting circuit 69. The power source controller 67 controls the power source circuit 68 upon receiving control signals from the power transmitting controller 76. The power source circuit 68 controls the power transmitting circuit 69 upon receiving control signals from the power source controller 67 and an electric power supply from an outer power source to be described later. The power transmitting circuit 69 is provided with a transmission coil (resonator) that generates an oscillating field M upon receiving an electric power supply from the power source circuit 68. This transmission coil will be described in [method of power transmitting/power receiving] to be described later.

The power receiving apparatus 41 of the wireless X-ray detector 4 generates electric power upon receiving the oscillating field M from the power transmitting apparatus 60. The device is provided with the wireless X-ray detector 4 and houses the power receiving apparatus 41; however, the device itself is configured without the power receiving apparatus 41. The power receiving apparatus 41 has a power receiving circuit 42, a charge circuit 43, and a power source circuit 44. The power receiving circuit 42 is provided with a reception coil (resonator) that generates electric power upon receiving the oscillating field M. The reception coil has a resonant frequency that is substantially equal to the transmission coil. The phrase "substantially equal" means to tolerate errors that do not cause problems in realizing power transmitting/power receiving using a magnetic resonance to be described later. The reception coil will be described in [method of power transmitting/power receiving] to be described later. The charge circuit 43 charges electric power generated by the power receiving circuit 42. As illustrated in FIG. 3, the charge circuit 43 is provided with a rectification circuit 431 and a battery 432. The rectification circuit 431 converts AC power generated by the power receiving circuit 42 into DC electric power. The battery 432 charges this DC electric power. The power source circuit 44 supplies electric power charged in the battery 432 to an X-ray detector 45, a signal processing part 46, a controller 47, and a transmitting and receiving part 49. The charge monitor 48 may be configured in such a manner that this electric power is also supplied thereto.

The X-ray detector 45 is an FPD. The signal processing part 46 applies predetermined processing to electric signals generated by the X-ray detector 45. This processing and the parameters thereof are decided based on the control signals input from a main controller 70 via transmitting and receiving parts 77, 49. The controller 47 controls the power source circuit 44, the signal processing part 46, the transmitting and receiving part 49, etc. The charge monitor 48 detects the charge level of the battery 432. The charge level is a ratio of, for example, the current charge amount of the battery 432 and the largest charge amount (preset value) of the battery 432. The charge monitor 48 may be configured such that it detects the current charge amount of the battery 432 and estimates the current charge amount based on the charge time and the intensity of the oscillating field M, etc. In the latter case, a charge monitor can be arranged on the body side. The transmitting and receiving part 49 performs wireless communication with the transmitting and receiving part 77. This wireless communication system is optional.

[Method of Power Transmitting/Power Receiving]

A method of power transmitting/power receiving using the power transmitting apparatus 60 and the power receiving apparatus 41 will be described.

This embodiment, using a transmission coil and a reception coil that resonate (resonance) at a frequency that is substantially equal, supplies non-contact electric power by resonance. A power supply method by magnetic coupling utilizing resonance is advantageous in that, compared to other methods using merely electromagnetic induction without resonance and electric waves, it can realize a non-contact power supply at a far distance (about 3 to 4 m) and a high output (about several W to several kW). Hereinafter, magnetic coupling utilizing resonance is referred to as "magnetic resonance." This is effective particularly for wireless devices of medical image diagnosis apparatuses. In addition, for an electric power supply by magnetic resonance, power transmitting/power receiving is possible even when the axes of both coils deviate slightly. This embodiment is also advantageous in that even if there is an obstacle between both coils, power transmitting/power receiving is possible and selective power supply to a plurality of devices is possible by differing resonant frequencies.

Figure 4:
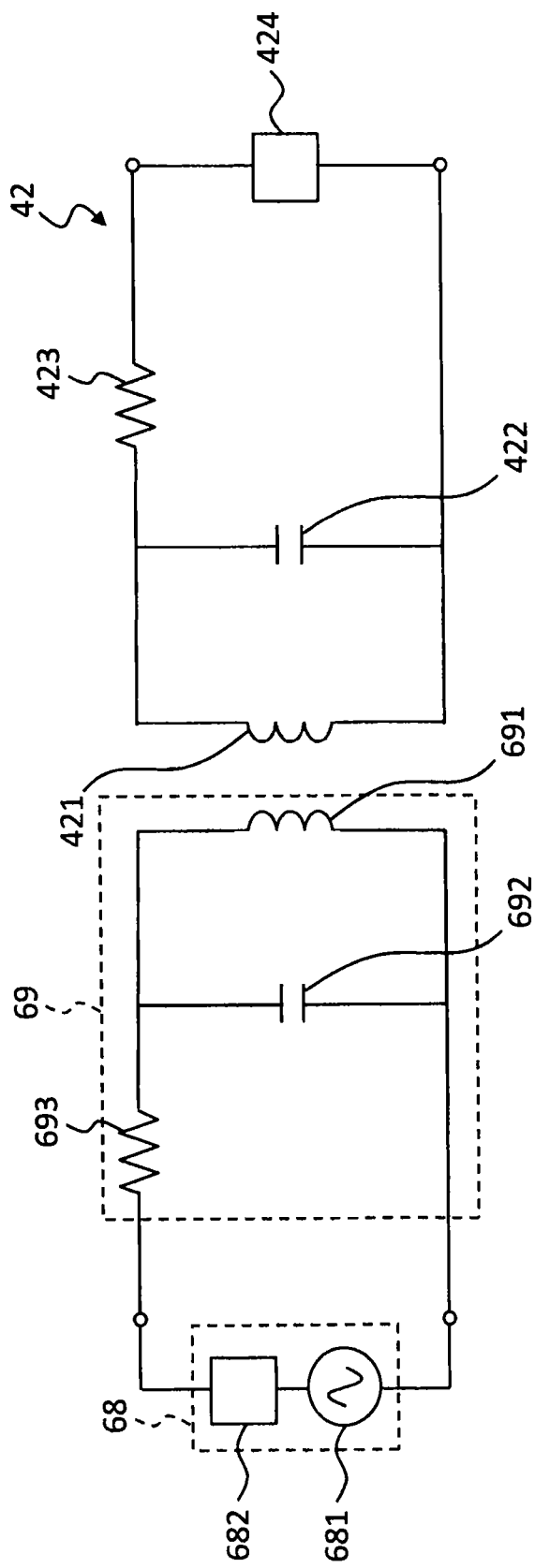
FIG. 4 illustrates an example of a circuit configuration of the medical image diagnosis apparatus according to the embodiment.

A summary of the circuit configuration of the power transmitting apparatus 60 and the power receiving apparatus 41 for realizing such a power transmitting/power receiving method is illustrated in FIG. 4.

The power source circuit 68 of the power transmitting apparatus 60 has an AC source 681 and an AC resistance 682 that provides inner resistance thereto. This AC source 681 may be a power source receiving a supply from the outside of the configuration illustrated in FIG. 2, or may be a power source separately provided for moving the body from the body side. Hereinafter, a power source received by the power transmitting apparatus 60 from the outside is referred to as an outer power source. This outer power source is at least an AC source to which the power transmitting apparatus 60 can transmit power separately from the body. In addition, the AC source may receive an AC source at a desired frequency from the outside, or may generate an AC source that is converted into a desired frequency upon receiving the AC source or a DC power source from the outside. In addition, separately from the AC source, the DC power source is needed in order for the power transmitting apparatus 60 to operate independently from the apparatus of the body, and the DC source receives a power supply as well as the AC source. Further, the DC power source may be taken from the AC source that receives the power supply. The AC source 681 preferably has a frequency higher than that of a commercial power source. The AC source 681 inputs electric power from the outer AC source in the power transmitting apparatus 60. A resistance 693 is used to heighten Q as a resonate circuit and match the AC source 681 and the resonate circuit. A power transmitting circuit 69 has a transmission coil 691 and a capacitor 692, and is a resonate circuit (resonator) that oscillates (namely, resonates) with a frequency of the power source supplied from the AC source 681. The transmission coil 691 generates an oscillating field upon receiving the power supply of the AC power.

The power receiving circuit 42 of the power receiving apparatus 41 has a reception coil 241, a resonate circuit composed of a capacitor 422, a resistance 423, and a load 424. The power receiving circuit 42 has a resonance frequency that is substantially equal to the power transmitting circuit 69. In other words, the resonate circuit on the transmission side and the resonate circuit on the receiving side have resonance frequencies that are substantially equal. According to such a configuration, non-contact an electric power supply using magnetic resonance becomes possible between the power transmitting apparatus 60 and the power receiving apparatus 41 that are arranged with an appropriate positional relation. Further, a reception coil 241 is arranged at a position such that it can efficiently receive a magnetic force (oscillating field) output from a transmission coil 691.

[Usage Pattern]

The usage patterns of the X-ray diagnosis apparatus configured as described above will be described.

(First Usage Pattern)

It is assumed that the power transmitting apparatus 60, specifically, the power transmitting apparatus 62 generates an oscillating field. When the user mounts the wireless X-ray detector 4 on the top plate 21, the power receiving circuit 42 generates electric power upon receiving this oscillating field. This electric power is transmitted to the rectification circuit 431 to be converted into DC electric power and charged in the battery 432. Once sufficiently charged, the user carries out the predetermined operation, stopping generation of the magnetic field by the power transmitting apparatus 62.

When the user instructs X-ray imaging to start by carrying out the predetermined operation, the main controller 70 transmits control signals to the wireless X-ray detector 4 via the transmitting and receiving part 77. The wireless controller 47 of the X-ray detector 4 controls the power source circuit 44 to supply electric power charged in the battery 432 to the X-ray detector 45, etc. If the X-rays are output from the X-ray tube 14, the X-ray detector 45 detects the X-rays transmitted through the test body and outputs electric signals. The signal processing part 46 applies the predetermined processing to these electric signals. The controller 47 transmits the data output from the signal processing part 46 to the main controller 70 via the transmitting and receiving parts 49, 77. The main controller 70 transmits this data to the image processing part 73. Then, applying the predetermined processing to this data, the image processing part 73 makes the display 75 display the images thereon and the image storage 74 store the image data.

Further, it is possible to provide a function to inform whether or not the wireless X-ray detector 4 is arranged at a position capable of supplying power in the wireless X-ray detector 4. As an example of this, a light source (LED, etc.) can be provided which is lit by electric power generated by the power receiving circuit 42. In addition, the power supply level may be informed by providing a plurality of light sources in which a certain number thereof are lit according to the power supply level (for conversion efficiency from the magnetic field to the electric power) and in which emission luminance is changed depending on the power supply level. The power supply level is, for example, detected by the charge monitor 48.

In addition, a function to indicate the charge level may be provided. The charge level is detected by the monitor 48. The charge level is indicated on an indicator provided to the wireless X-ray detector 4 and the body. The indicator provided to the wireless X-ray detector 4 includes a light source and a display device (LCD, etc.). In addition, the indicator provided to the body includes (the LCD, etc. of) the imaging condition input part 13 and the display 75. Further, the charge level of the battery 432 and the remaining amount have the same concepts.

(Second Usage Pattern)

In this usage pattern, the control for stopping the power supply according to the start trigger of the X-ray imaging will be specifically described. This start trigger includes (1) the input of patient information into the body, (2) execution of the operation for instructing the start of the check, (3) arrangement of the device at a predetermined position, etc. An X-ray diagnosis apparatus according to this embodiment has a first detector for detecting the start trigger of the X-ray imaging.

The control based on the input of (1) patient information will be described. The input of patient information is carried out using a console (not illustrated). The console transmits signals to the main controller 70 at an arbitrary timing from the start of input of patient information until the end thereof. Upon receiving this signal, the main controller 70 stops the operation of the power transmitting apparatus 62 via the power transmitting controller 76. Thereby, the power supply to the wireless X-ray detector 4 is stopped. Further, in the event that the charge level is no more than a threshold, the present embodiment can be configured such that this is informed. The first detector in this case is the console or the main controller 70.

(2) The control based on the instructions on the start of the check will be described. The instructions of the start of the check are carried out by operating the imaging condition input part 13 and the console, or a dedicated imaging start switch (not illustrated). If the operation for starting the imaging is carried out, an operation signal thereof is input to the main controller 70. Upon receiving this operation signal, the main controller 70 stops the power supply in the same manner as described above. The first detector in this case is the main controller 70.

(3) The control based on the fact that the device is arranged at a predetermined position will be described. In this example, in addition to the above-described configuration, a sensor, a switch, etc. are disposed at these predetermined positions, respectively. Specifically, a micro switch, etc. is disposed. In addition, at this predetermined position, the FPD holder 51, 52, the top plate 21, etc. are cited.

The above-described sensor, etc. detect when the wireless X-ray detector 4 is arranged at a predetermined position while transmitting a detection signal to the main controller 70. Upon receiving this detection signal, the main controller 70 stops the power supply in the same manner as described above. The first detector in this case includes the above-described sensor, etc.

(Third Usage Pattern)

According to this usage pattern, the control for supplying power only when the X-ray imaging is not actually carried out. Specifically, the control for starting the power supply according to the ending trigger of the X-ray imaging will be described. This ending trigger includes (1) the ending of the processing relevant to the check, (2) execution of the operation for instructing the ending of the check, (3) execution of the operation for powering off the body or the device, (4) the absence of an operation to the body or the device for more than a predetermined time, etc. The X-ray diagnosis apparatus according to this usage pattern has a second detector for detecting the ending trigger of the X-ray imaging.

(1) The control based on ending the processing relevant to the check will be described. Exemplary processing relevant to the check includes the projection of X-rays from the X-ray tube 14, detection of X-rays by the X-ray detector 45, the image processing image by the processing part 73, etc. The control of the X-ray tube 14 and the image processing part 73 are managed by the main controller 70. The main controller 70 completes the control of the X-ray tube 14, etc., subsequently starting the operation of the power transmitting apparatus 62 via the power transmitting controller 76. Thereby, the power supply to the wireless X-ray detector 4 is started. The second detector in this case is the main controller 70.

(2) The control based on the operation for instructing the ending of the check will be described. This check is carried out by operating the imaging condition input part 13 and the console, or a dedicated imaging start switch (not illustrated). If the operation for ending the imaging is carried out, an operation signal thereof is input to the main controller 70. Upon receiving this operation signal, the main controller 70 starts the power supply in the same manner as described above. The second detector in this case is the main controller 70.

(3) The control based on the operation for powering off will be described. The powering off operation of the body is carried out by operating the imaging condition input part 13, the console, and a dedicated power source switch (not illustrated). The powering off operation of the wireless X-ray detector 4 is carried out using the power source switch (not illustrated). If the powering off operation of the body is carried out, an operation signal thereof is transmitted to the main controller 70. Upon receiving this operation signal, the main controller 70 carries out the processing for ending the power source supply to respective parts of the apparatus and the processing for starting the power supply in the same manner as described above, after which it turns off the power source. The second detector in this case is the main controller 70. Further, even if the power source of the body is turned off or the power source of the wireless X-ray detector 4 is turned off, the supply of the DC power source is received from the outer power source such that the power transmitting apparatus 60, the power receiving apparatus 42, and the charge circuit 43 are operated.

On the other hand, when the power source off operation of the wireless X-ray detector 4 is carried out, an operation signal thereof is transmitted to the controller 47. Upon receiving this operation signal, the controller 47 transmits signals to the main controller 70 via the transmitting and receiving parts 49, 77. Upon receiving this signal, the main controller 70 starts the power supply in the same manner as described above. In this case, the processing for ending the power source supply to respective parts of the apparatus may be carried out. The second detector in this case is the controller 70 or the main controller 70.

(4) The control based on the absence of any operation for more than a predetermined time will be described. The main controller 70 has a timer (timer) (not illustrated). For example, a microprocessor is responsible for the function of this timer. Every time an operation is carried out, namely, every time operation signals from respective parts of the apparatus are input, the main controller 70 resets the timer. If the measured time on the timer reaches a predetermined time, the main controller 70 starts the power supply in the same manner as described above. The second detector in this case is the main controller 70.

(Fourth Usage Pattern)

In this usage status, the case of controlling the charge level depending on the power supply will be described. As described above, the charge level is detected by the charge monitor 48 (3rd detector). The charge monitor 48 transmits the detection results of the charge level to the main controller 70 via the transmitting and receiving parts 49, 77 at predetermined time intervals. The main controller 70 determines whether or not these detection results are no more than a predetermined first level. In the event that the detection results are no more than the first level, the main controller 70 starts the power supply in the same manner as described above.

The charge monitor 48 may determine whether or not the charge level is no more than the first level. In this case, the charge monitor 48 can be configured such that it transmits signals to the main controller 70 only when the charge level is no more than the first level.

On the contrary, when the detection results of the charge level are no less than a predetermined second level (for example, the largest charge amount), the charge monitor 48 can also be configured such that it stops the power supply. This determination is carried out by the main controller 70 or the controller 47. In addition, when a condition such as the remaining imaging time can be estimated, this calculated second level can be determined as determination criteria by calculating the second level based on this condition.

(Fifth Usage Pattern)

In this usage status, the case of controlling the distance between the power transmitting apparatus 60 and the power receiving apparatus 41 (the wireless X-ray detector 4) depending on the power supply will be described. The X-ray diagnosis apparatus according to this usage pattern has a determination part that determines whether or not this distance is no more than a predetermined distance. The determination part may be configured such that it (1) always monitors this distance and compares the detection results of the distance to a threshold, and the determination part may be configured such that it (2) detects that the power receiving apparatus 41 is arranged on the field at no more than a predetermined distance from the power transmitting apparatus 60.

The continuous monitoring function in (1) is carried out, for example, by a TV camera for imaging the inside of the laboratory and the main controller 70. Upon analyzing the images taken by the TV camera and detecting the position of the wireless X-ray detector 4, the main controller 70 in this case derives the distance between this position and the position of the predetermined power transmitting apparatus 60. Further, the comparison processing in (1) is carried out by the main controller 70. When this distance is no more than a predetermined distance, the main controller 70 starts the power supply in the same manner as described above. The determination part in this case is configured by the main controller 70 and the TV camera. Further, the means of continuous monitoring and the means for carrying out comparison processing are not limited to the above-described configuration, with any technology capable of realizing these functions also being suitable.

The detection processing in (2) can be carried out by the TV camera and the main controller 70. Specifically, the TV camera may be arranged and set such that it only images the field at no more than a predetermined distance from the power transmitting apparatus 60. Upon analyzing the image taken by the TV camera, the main controller 70 determines whether or not the wireless X-ray detector 4 is drawn in this imaging field. Once the wireless X-ray detector 4 is determined as being drawn, the main controller 70 starts the power supply in the same manner as described above. The determination part in this case is configured by the main controller 70 and the TV camera. The means for carrying out the above-described detection processing is not limited to the above-described configuration, with any technology capable of realizing these functions also being suitable. For example, a sending part for sending signals of predetermined intensities (electric waves, etc) is provided in the wireless X-ray detector 4 in addition to a receiving part for receiving these signals provided in the power transmitting apparatus 60. Then, the main controller 70 can be configured such that it starts the power supply according to the fact that the intensities of the signals to be received by the receiving part are no less than a predetermined level. On the contrary, the main controller 70 can be also configured such that it stops the power supply according to the fact that the intensities of the signals to be received by the receiving part are no more than a predetermined level.

[Effect]

The effects of the X-ray diagnosis apparatus according to this embodiment will be described. The X-ray diagnosis apparatus according to the embodiment is a medical image diagnosis apparatus that receives signals from the test body and derives images in the test body (the organization information). This X-ray diagnosis apparatus has a body, a power transmitting apparatus 60, and a wireless X-ray detector 4 (device) including a power receiving apparatus 41. The power transmitting apparatus 60 has a transmission coil 691 (power transmitting circuit 69) that receives electric power from the outside and generates an oscillating field. The power receiving apparatus 41 includes a reception coil 241 (power receiving circuit 42) that has a resonant frequency substantially equal to that of the transmission coil 691, and upon receiving the oscillating field generated by the transmission coil 691, generates electric power. The wireless X-ray detector 4 is operated using the electric power generated by the reception coil 241.

According to such an X-ray diagnosis apparatus, as electric power can be supplied to the wireless X-ray detector 4 by a power supply method using magnetic resonance, electric power to the device can be preferably supplied in liaison with the body. Specifically, for example, compared to the magnetic supply from a mere coil, effects can be derived wherein, power can be supplied even at a far distance and with high output (approximately several W to several kW), even if the axes of both coils slightly deviate, and even if there is an obstacle between the coils. In addition, as the conventional power supply method, the wireless X-ray detector 4 does not need to be connected to the dedicated charger or to be closed thereto. Thereby, the risk of the battery 432 charge being neglected can be reduced. In addition, there is no trouble regarding connecting or approximating the wireless X-ray detector 4 to the dedicated charger, thereby improving the operability.

In addition, according to this embodiment, the power transmitting apparatus 60 is arranged on the body as well as on the floor, on the ceiling, on the wall, etc. of the laboratory. Further, the power transmitting apparatus 60 is disposed in the vicinity of the position at which the wireless X-ray detector 4 is arranged at the time of checking. This "vicinity" is the distance at which it is possible to supply power at least by magnetic resonance. This configuration makes it possible to reduce the risk of the battery 432 charge being neglected.

In addition, the wireless X-ray detector 4 (device) according to this embodiment has a battery 432 for charging electric power generated by the power receiving circuit 42, and is operated (detection of the X-rays, image processing, etc.) using the electric power charged in this battery 432. Thus, upon mounting the battery on the device, the power transmitting apparatus 60 does not need to be continuously operated.

In addition, the X-ray diagnosis apparatus according to this embodiment has an indicator for indicating the remaining battery level of the battery 432. Thereby, the user can see the remaining battery level of the battery 432 and start or end charging as necessary.

In addition, the main controller 70 according to this embodiment carries out a power supply check only when a check (X-ray imaging) by the body or the device has not been carried out. If the power is supplied during the check, there is a possibility that the oscillating field M generated by the power transmitting apparatus 60 may adversely affect the check. Potential adverse effects include malfunctions of the body and the device. Further, the main controller 70 thus operated is included in a "controller."

In addition, the X-ray diagnosis apparatus of this embodiment has a first detector for detecting the start trigger of the check, and stops the supply of electric power to the power transmitting apparatus 60 corresponding to detection of this start trigger. In other words, the main controller 70 determines whether or not the electric power should be generated depending on the presence or absence of input of the start trigger. Thereby, the power supply to the wireless X-ray detector 4 is stopped. In other words, when the start trigger is input, stopping generation of the oscillating field, the generation of electric power is stopped. Due to such a configuration, a control for supplying power only when the check has not been carried out is realized. Further, the start trigger indicates the timing corresponding to the start of the check, as well as the preparation for the check. The start trigger includes at least one of patient information input into the body, execution of the operation for instructing the start of the check, and arrangement of the device at a predetermined position, in addition to indicating the status of the body. This first detector is cited as an example of the status checker.

In addition, the X-ray diagnosis apparatus according to this embodiment has a second detector for detecting the ending trigger of the check, and starts the supply of electric power to the power transmitting apparatus 60 corresponding to detection of this ending trigger. In other words, the main controller 70 determines whether or not electric power should be generated depending on the presence or absence of input of the ending trigger. Thereby, the power supply to the wireless X-ray detector 4 is started. In other words, when the start trigger is input, generating the oscillating field, the generation of electric power is started. Due to such a configuration, a control for supplying power only when a check has not been carried out is realized. Further, the ending trigger indicates the timing corresponding to the ending of the check, the preparation thereof, or processing after the ending of the check. The ending trigger includes at least one of the ending of the processing relevant to the check, execution of the operation for instructing the ending of the check, execution of the power source off operation of the body or the device, and the absence of an operation to the body and the device for more than a predetermined time, in addition to indicating the status of at least one of the body or the device. This second detector is cited as an example of the status checker.

In addition, the X-ray diagnosis apparatus according to this embodiment has a third detector for detecting the charge level of the battery 432 as an example of the status of the device, and a main controller 70 that controls the supply of electric power to the power transmitting apparatus 60 based on the detection results of this charge level. This control includes at least one of the starting of the power supply corresponding to lowering of the charge level (remaining battery level), and the stopping of the power supply corresponding to the fact that the charge level becomes sufficient.

According to the former, the main controller 70 determines whether or not the electric power should be generated based on the charge level. Then, when the charge level is lowered to a predetermined standard, it determines that the electric power should be generated, and the electric power is generated by generating an oscillating field. It is possible to prevent the case in which the check is stopped because the charge level of the battery 432 is largely lowered. In addition, there is no need to worry about the timing for charging the battery 432. On the other hand, according to the latter, the main controller 70 determines whether or not the power supply should be stopped based on the charge level. Then, when the charge level is lowered to a predetermined standard, it determines that the electric power should be stopped, and the power supply is stopped by stopping the oscillating field. Effects such as preventing overcharging of the battery 432 and saving on electricity can be achieved.

Further, the main controller 70 thus operated corresponds to an example of "the controller." The third detector is cited as an example of the status checker. As an example of the status checker, the first to third detectors are cited and described; however, the status checker may be configured by not only one of these but also by plural detectors. According to the above-described configuration, the status checker checks on the status of at least the body and the device.

In addition, the X-ray diagnosis apparatus according to this embodiment has a determination part that determines whether or not the distance between the power transmitting apparatus 60 (transmission coil) and the wireless X-ray detector 4 is no more than a predetermined distance, in addition to a main controller 70 that controls the supply of electric power to the power transmitting apparatus 60 based on the determination results of the distance. This control includes at least one of the control that supplies power when this distance is no more than the predetermined distance, and the control that does not supply power when this distance exceeds the predetermined distance. The former includes at least one of the starting of the power supply corresponding to the fact that this distance is shifted to a distance no more than the predetermined distance, and the control that starts the power supply when this distance detected at optional timing is no more than the predetermined distance power supply. On the other hand, the latter includes at least one of the stopping of the power supply corresponding to the fact that, when this distance is monitored, this distance exceeds the predetermined distance, and the control that stops the power supply when this distance detected at optional timing exceeds a predetermined distance. According to such a control, it is possible to automatically start the power supply depending on the arrangement and movement of the wireless X-ray detector 4, making this embodiment more convenient.

Further, in this embodiment, the power supply to the wireless X-ray detector 4 has been described; however, the targets of the power supply are not limited to this. For example, this embodiment can be configured such that it supplies power to an actuator in order to expand and contract the support mechanism 12, the display device, an actuator to drive the diaphragm of the X-ray limiting device 15, and an actuator of the supine position imaging table 2 and/or the upright position imaging table 3.

In addition, the X-ray diagnosis apparatus according to this embodiment is provided with a plurality of power transmitting apparatuses 61 to 66 that are arranged at different positions, respectively. According to such a configuration, it is possible to supply power to the wireless X-ray detector 4 arranged at various positions in the laboratory.

Further, it is possible to simultaneously supply power to the wireless X-ray detector 4 arranged at a certain position by two or more of the power transmitting apparatuses 61 to 66. For example, it is possible to simultaneously supply power to the wireless X-ray detector 4 fitted to FPD holder 51 by the power transmitting apparatus 63 and the power transmitting apparatus 65. In addition, by horizontally arranging the wireless X-ray detector 4 in the vicinity of the FPD holder 52, namely, by approximately-horizontally arranging the axis of the reception coil 421 to the axes of the transmission coils 691 of respective power receiving apparatuses 61, 66, it is possible to simultaneously supply power to the wireless X-ray detector 4 by the power transmitting apparatus 61 and the power transmitting apparatus 66. According to such a power supply method, simultaneously receiving the oscillating field generated by two or more of the power transmitting apparatuses 61 to 66, the power receiving apparatus 41 can generate electric power, allowing it to supply power more quickly than in the case of only using one power transmitting apparatus (in other words, rapid charging can be carried out). Further, by selecting some of the power transmitting apparatuses 61 to 66 depending on the arrangement of the wireless X-ray detector 4 (for example, the wireless X-ray detector 4 arranged comparatively close to this arrangement position), the main controller 70 can operate only the selected power transmitting apparatus.

MODIFICATION EXAMPLE

The embodiment of this invention is not limited to the above-described embodiment. Hereinafter, various modification examples will be described. Further, various configurations of the above-described embodiment and the following various modification examples can be appropriately combined.

Modification Example 1

Figure 5:
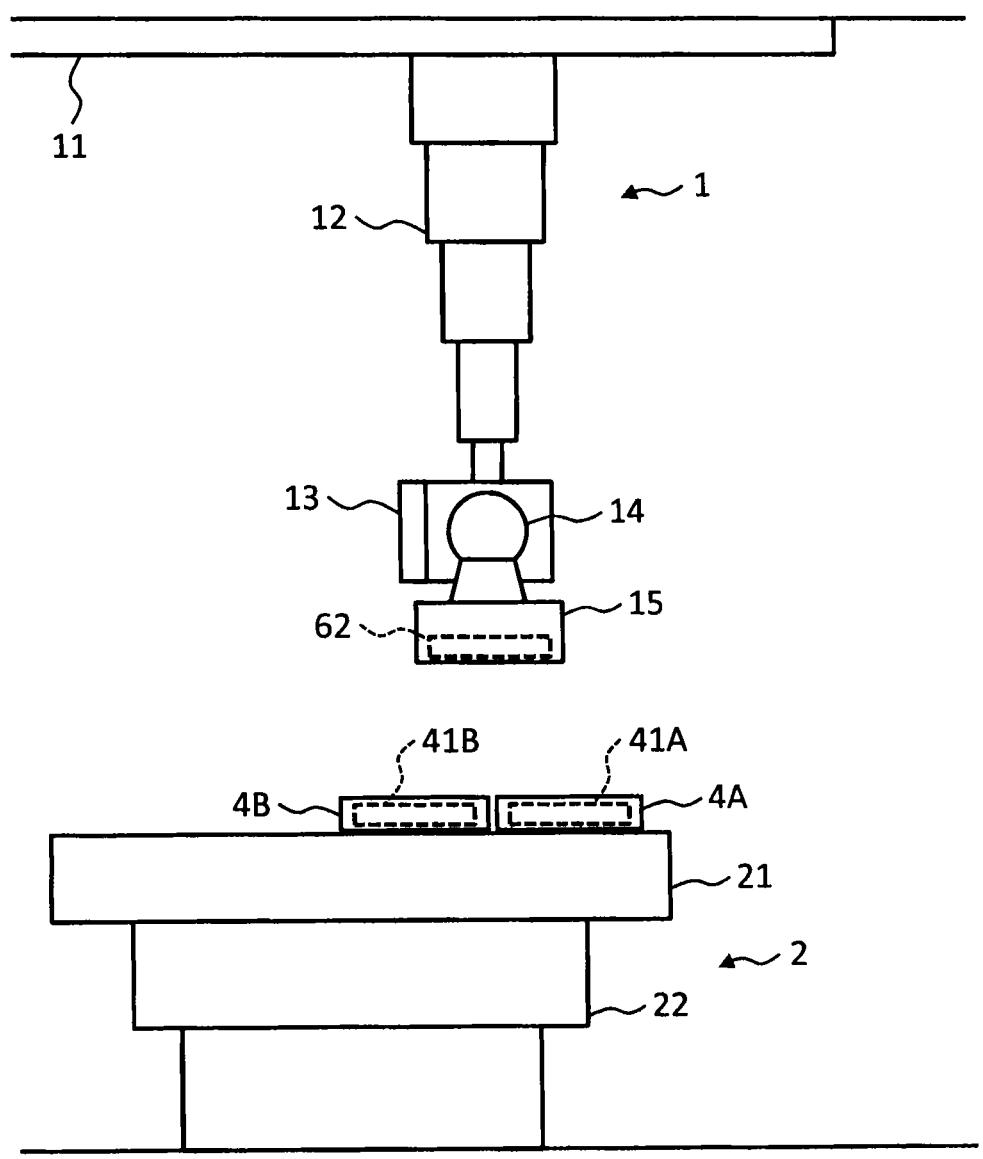
FIG. 5 illustrates an example of a configuration of the medical image diagnosis apparatus according to a modification example.

The medical image diagnosis apparatus (X-ray diagnosis apparatus) according to the modification example is illustrated in FIG. 5. The body of the X-ray diagnosis apparatus according to the modification example is configured in the same manner as the above-described embodiment. Further, FIG. 5 only illustrates part of the configuration of the body illustrated in FIG. 1. In addition, as the device according to the modification example, two wireless X-ray detectors 4A, 4B are used. Each wireless X-ray detector 4 has the same configuration as that of the wireless X-ray detector 4 according to the above-described embodiment. Particularly, the wireless X-ray detector 4A has a power receiving apparatus 41A, while the wireless X-ray detector 4B has a power receiving apparatus 41B.

The user arranges two wireless X-ray detectors 4A, 4B at the optional positions suitable for the power supply. In FIG. 5, two wireless X-ray detectors 4A, 4B are arranged on the top plate 2 and below the power transmitting apparatus 62. In this state, supplying electric power to the power transmitting apparatus 62, both power receiving apparatuses 41A, 41B generate electric power by the oscillating field generated by the power transmitting apparatus 62, and the generated electric power is charged in both batteries (not illustrated).

Such a method is realized by a property of the power supply method using magnetic resonance, in particular, the fact that supplying power at a far distance is possible, as well as the fact that supplying power is possible even if the axes of the coils on the power transmitting side and the power supply side slightly deviate. Further, the number of wireless X-ray detectors 4 to be simultaneously supplied power by one power transmitting apparatus 60 is not limited to two.

Thus, the X-ray diagnosis apparatus according to the modification example is provided with two or more wireless X-ray detectors (device), and two or more power receiving apparatuses (reception coil) included in these devices generate electric power while receiving the oscillating field generated by one power transmitting apparatus (transmission coil). Thereby, an effect can be derived, in which, in the medical image diagnosis apparatus having a plurality of devices arranged, the power can be simultaneously supplied to two or more devices.

Modification Example 2

In the above-described embodiment, a configuration in which power is supplied to the device with the battery using the magnetic resonance, namely, a configuration of charging the battery of the device via non-contact has been described. In this modification example, the case in which the device is not provided with a battery will be described. Further, in this case, it is necessary to continuously supply power during operation of the device.

The configuration of the body is similar to that of the above-described embodiment even when the device is not provided with a battery (for example, refer to FIG. 1, FIG. 2). When the device is a wireless X-ray detector, the configuration illustrated in FIG. 3 with the battery 432 removed can be applied. In other words, a configuration can be applied in which AC power generated by the power receiving circuit 42 is converted into DC electric power by the rectification circuit 431, and the power source circuit 44 supplies this DC electric power to the X-ray detector 45, etc.

According to this modification example, electric power is supplied to the wireless X-ray detector 4 at least during the check (during the X-ray imaging). For example, upon receiving the "start trigger" of the above-described embodiment, the main controller 70 starts supplying electric power to the power transmitting apparatus 60. Thereby, the power supply from the power transmitting apparatus 60 to the wireless X-ray detector 4 is started. In addition, upon receiving the "ending trigger" of the above-described embodiment, the main controller 70 stops supplying electric power to the power transmitting apparatus 60. Thereby, the power supply from the power transmitting apparatus 60 to the wireless X-ray detector 4 is stopped.

According to this modification example, it is possible to preferably supply electric power to the device without a battery. Further, in this modification example, in order to avoid adverse effects of the magnetic field on the body, etc., during the check, the power transmitting apparatus 60 can be disposed very near the position where the wireless X-ray detector 4 is arranged. For example, among the power transmitting apparatuses 61 to 66 illustrated in FIG. 1, the power transmitting apparatus 62 can be arranged near the top plate 21 while the power transmitting apparatuses 63, 64 can be respectively arranged near the FPD holders 51, 52.

Modification Example 3

Application of the above-described embodiment and modification examples to medical image diagnosis apparatuses other than the X-ray diagnosis apparatus will be described. As described above, an MRI apparatus and an ultrasound diagnosis apparatus are included as such a medical image diagnosis apparatus.

The device in the MRI apparatus is, for example, a high frequency coil unit. For example, as described in Japanese published unexamined application No. 2010-207464, a high frequency coil unit is fitted at a predetermined region (head, etc.) of the test body during the check. It is possible to apply a configuration relevant to the power supply described in the above-described embodiment and the modification example to the high frequency coil unit.

The device in the ultrasound diagnosis apparatus is, for example, an ultrasound probe. The ultrasound probe projects ultrasound waves to the test body, while receiving reflected waves from the test body. Further, the ultrasound probe includes a wired ultrasound probe and a wireless ultrasound probe (for example, refer to Japanese published unexamined application No. 2008-000406); however, the configuration relevant to the power supply described in the above-described embodiment and the modification example can be applied to both of these ultrasound probes. Further, the configuration relevant to the power supply described in the above-described embodiment and the modification example can be applied to the medical image diagnosis apparatus and devices other than these.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image diagnosis apparatus that receives signals from a test body and derives organization information thereof so as to check the test body, comprising:
 a body;
 a power transmitting circuit having a transmission coil housed in the body, receiving electric power from the outside and generating an oscillating field due to resonance from the transmission coil;
 a power receiving circuit having a reception coil that resonates at a frequency substantially equal to the resonant frequency of the transmission coil and generates electric power upon receiving the oscillating field generated by the transmission coil;
 a device that houses the power receiving circuit and operates by electric power from the power receiving circuit via non-contact with the body so as to derive the organization information;
 a status checker configured to derive at least one of the operation statuses of the body and the device; and
 a controller configured to determine whether or not the electric power should be generated depending on at least one of the statuses of the body and the device, and based on the determination results, to control the generation of the electric power by the transmission coil.

2. The medical image diagnosis apparatus according to claim 1, wherein the device is a wireless X-ray detector of an X-ray diagnosis apparatus, a high frequency coil unit of an MRI apparatus, or an ultrasound probe of an ultrasound diagnosis apparatus.

3. The medical image diagnosis apparatus according to claim 1, wherein the power transmitting circuit comprises the transmission coil and first capacitor so as to generate resonance, while the power receiving circuit comprises the reception coil and second capacitor so as to generate resonance.

4. The medical image diagnosis apparatus according to claim 1, wherein the device has a battery for storing the electric power generated by the reception coil and operates using the electric power stored in the battery.

5. The medical image diagnosis apparatus according to claim 4, further comprising an indicator configured to indicate the remaining power level of the battery.

6. The medical image diagnosis apparatus according to claim 1, comprising the two or more devices, wherein the two or more power receiving circuits included in the two or more devices receive an oscillating field generated by the one power transmitting circuit to generate electric power.

7. The medical image diagnosis apparatus according to claim 4, wherein the status checker has a first detector configured to detect the start trigger of the check, and
 the controller is configured to stop the supply of electric power by the power transmitting circuit according to detection of the start trigger.

8. The medical image diagnosis apparatus according to claim 7, wherein the start trigger includes at least one of the input of patient information into the body, execution of the operation for instructing start of the check, and arrangement of the device at a predetermined position.

9. The medical image diagnosis apparatus according to claim 4, wherein the status checker has a second detector for detecting ending of the trigger of the check, and
 the controller is configured to start the supply of electric power by the power transmitting circuit according to detection of the start trigger.

10. The medical image diagnosis apparatus according to claim 9, wherein the ending trigger includes at least one of the ending of the processing relevant to the check, execution of the operation for instructing the ending of the check, execution of the operation for the powering off of the body or the device, and the absence of operation to the body and the device for more than a predetermined time.

11. The medical image diagnosis apparatus according to claim 4, wherein the status checker has a third detector for detecting the charging level of the battery, and
   the controller is configured to control the supply of electric power by the power transmitting circuit based on the detection results of the charging level.

12. The medical image diagnosis apparatus according to claim 1, wherein the controller is configured to detect whether or not the distance between the transmission coil and the device is no more than a reference distance.

13. The medical image diagnosis apparatus according to claim 1, comprising a plurality of the power transmitting circuits arranged at different places, respectively.

14. The medical image diagnosis apparatus according to claim 13, wherein the power receiving circuit receives the oscillating fields generated by no more than two of the plurality of power transmitting circuits at the same time to generate electric power.

\* \* \* \* \*